United States Patent [19]

Neckers et al.

[11] Patent Number: 6,166,233

[45] Date of Patent: Dec. 26, 2000

[54] ONIUM GALLATES CATIONIC INITIATORS

[75] Inventors: Douglas C. Neckers, Perrysburg; Alexandre Mejiritski; John Malpert, both of Bowling Green, all of Ohio

[73] Assignee: Spectra Group Limited, Inc., Maumee, Ohio

[21] Appl. No.: 09/375,857

[22] Filed: Aug. 17, 1999

[51] Int. Cl.$^7$ .................................. C07F 5/00; C08F 2/46
[52] U.S. Cl. .................................. 556/1; 556/28; 522/25; 522/29
[58] Field of Search .......................... 556/1, 28; 522/25, 522/29

[56] References Cited

U.S. PATENT DOCUMENTS

| | | | |
|---|---|---|---|
| 5,340,898 | 8/1994 | Cavezzan et al. | 528/19 |
| 5,639,802 | 6/1997 | Neckers et al. | 522/25 |

OTHER PUBLICATIONS

Eaton, "Dye Sensitized Photopolymerization", *Advances in Photochemistry*, vol. 13, pp. 427–487 (1986) John Wiley & Sons.

Chatterjee et al., "Electron–Transfer Reactions in Cyanin Borate Ion Pairs: Photopolymerization Initiators Sensitive to Visible Light", *J. Am. Chem. Soc.*, vol. 110, pp. 2326–2329 (1988).

Hassoon et al., "Electron Transfer Photoreduction of 5,7–Diiodo–3–butoxy–6–fluorone with Tetrabutylammonium Triphenylbutylborate and N,N–Dimenthyl–2,6–diisopropylaniline", *J. Phys. Chem.*, 99, pp. 9416–9424 (1995).

*Primary Examiner*—Porfirio Nazario-Gonzalez
*Attorney, Agent, or Firm*—Thompson Hine & Flory LLP

[57] ABSTRACT

The present invention relates to novel onium gallates or gallates of organometallic compounds and polymerizable compositions containing the same. The onium gallates include an anionic gallate moiety and a cationic moiety. The anionic gallate moiety has the formula $$GaX_aR_b^-$$

in which X is a halogen or a hydroxy group, R is an aryl group, a and b represent integers ranging from 0 to 4 and the sum of a and b is 4. The cationic moiety is selected from the group consisting of iodonium, pyrylium, thiapyrylium, sulphonium, phosphonium, ferrocenium, and diazonium ions. The novel onium gallates are useful as cationic initiators of polymerization.

9 Claims, No Drawings

ONIUM GALLATES CATIONIC INITIATORS

BACKGROUND OF THE INVENTION

The present invention relates to novel onium gallates or gallates of organometallic complexes which are cationic initiators of polymerization, and to the use of such novel gallates for the polymerization or crosslinking of functional polymers or monomers by photochemical activation, or activation under an electron beam.

Onium salts or salts of organometallic complexes are well known as initiators of the cationic polymerization of monomers or of polymers substituted by functional groups of the epoxy or vinyl ether type, and any other cationically polymerized media and the like (U.S. Pat. Nos. 4,069,094; 4,450,360; 4,576,999 and 4,640,967; Canadian Patent No. 1,274,646; European Application EP-A-203,829). It has been observed that the best results are obtained when the anion of the initiator salt is $SbF_6^-$; or tetrakispentafluorophenyl borate, $(C_6F_5)_4B^-$.

SUMMARY OF THE INVENTION

The onium gallates of the present invention include a cationic moiety and an anionic gallate moiety. The cationic moiety is typically a diaryliodonium cation but it could also be any of the cations of other onium salts such as iodonium, pyrylium, thiapyrylium, sulphonium, phosphonium, ferrocenium or diazonium ions and the like.

The anionic gallate moiety has the formula $$GaX_aR_b^-$$

in which a and b are integers ranging from 0 to 4 with a+b=4, X is halogen or hydroxy, and R is an aryl group. More particularly, each X is a halogen atom (e.g., chlorine or fluorine) when a is 0, 1, 2, or 3 or an OH functional group when a is 0, 1, or 2; the symbols R, which may be identical or different, represent a phenyl group substituted by at least one electron-withdrawing group, especially a halogen atom (most particularly fluorine), $CF_3$, $NO_2$, CN and the like; or are an aryl radical containing at least two aromatic ring members, such as biphenyl, naphthyl and the like, optionally substituted by at least one element or one electron-withdrawing group, especially a halogen atom (most particularly fluorine), $CF_3$, $NO_2$, CN and the like. The invention also provides cationically polymerizable compositions containing the onium gallates.

DETAILED DESCRIPTION

Exemplary gallate anions include: $[Ga(C_6F_5)_4]^-$, $[Ga(C_6H_4CF_3)_4]^-$, $[(C_6F_5)_2GaF_2]^-$, $(C_6F_5GaF_3)^-$, $[Ga(C_6H_3F_2)_4]^-$.

Representative onium cations are described in detail in U.S. Pat. Nos. 5,550,265 and 5,340,898 to Rhone-Poulenc Chimie and U.S. Pat. No. 5,639,802 to Spectra Group Limited and include iodonium, pyrylium, thiapyrylium, sulphonium, phosphonium, ferrocenium and diazonium ions. Particularly preferred cations are aryliodonium ions such as 4-octyloxyphenylphenyl iodonium (OPPI), 4,4'-dimethyldiphenyliodonium, 4(3-trimethylsilylpropyloxy) phenylphenyl iodonium and diphenyliodonium; and sulphonium ions including triarylsulphonium ions such as triphenyl sulphonium ion and diphenyl 4 octyloxyphenyl sulphonium ion. Other sulphonium ions and associated sensitizers are described in Toba, Y. et al. *Macromolecules* Vol. 32, 3209–3215,1999.

The initiator salts of the present invention can be prepared by an exchange reaction between a salt of the cationic moiety (halide such as chloride, iodide and the like, hexafluorophosphate, tetrafluoroborate, tosylate and the like) and an alkali metal salt (e.g., sodium, lithium or potassium) of the anionic moiety. The operating conditions, respective amounts of reactants, choice of solvents, duration, temperature, stirring and the like are easily determined by one skilled in this art. They must permit recovery of the desired initiator salt in the solid state, by filtration of the precipitate formed or in the oily state by extraction using a suitable solvent.

The alkali metal salts of the anionic moiety can be prepared in known manner, by an exchange reaction between a halogallate compound and an organometallic compound (e.g., magnesium, lithium, tin, cadmium, copper, zinc and the like) bearing the desired hydrocarbon groups, in a stoichiometric amount, optionally followed by a hydrolysis using an aqueous solution of alkali metal halide. This type of synthesis is analogous to that described in *J. of Organometallic Chemistry*, Vol. 178, p.1–4, (1979); J.A.C.S., 82, 5298 (1960); *Anal. Chem. Acta*, 44, 175–183 (1969); U.S. Pat. No. 4,139,681 and DE-A-2,901,367; *Zh. Org. Khim.*, Vol. 25, No. 5—pages 1099–1102, (May 1989).

The preparation of salts of the onium ion is described in the literature. Reference can be made to the Rhone-Poulenc and Spectra Group patents referenced above.

The initiator salts of the present invention are useful for polymerizing or crosslinking, by radiation (especially under ultraviolet light or electron beam) monomers or polymers bearing functional groups such as epoxy groups, vinyl ether groups, and any cationically polymerizable monomers and the like. Generally, cationically polymerizable monomers and prepolymers are disclosed in U.S. Pat. No. 5,639,802, which is incorporated herein be reference. The monomers can be made monofunctional, difunctional and multifunctional. These may also be large molecular weight prepolymers and oligomers. Examples of cationically polymerizable compounds further include epoxy compounds, vinyl or allyl monomers, vinyl or allylic prepolymers, vinyl ethers, vinyl ether functional prepolymers, cyclic ethers, cyclic esters, cyclic sulfides, melamine formaldehyde, phenolic formaldehyde, cyclic organosiloxanes, lactanes and lactones, cyclic acetals and epoxy functional silicone oligomers. The gallates of the organometallic complexes can additionally be used as thermal polymerization initiators.

Representative examples of compositions which may be polymerized using the onium gallates of the present invention are described in U.S. Pat. No. 5,639,802. In addition, these may include bis-phenol-A-epoxy resins, cycloaliphatic epoxides, epoxidized olefins such as polybutadiene epoxide, epoxidized organic oils such as epoxidized soybean oil and the like. Cationically crosslinkable polyorganosilooxanes curable with the onium gallates of the invention are described in U.S. Pat. No. 5,340,898 which is incorporated herein by reference.

The onium gallate is added to the cationically polymerizable material in an amount sufficient to initiate polymerization or crosslinking and generally ranges from about 0.01 to 20 parts by weight per 100 parts by weight of the polymerizable material.

The compositions of the invention are useful as radiation polymerizable coatings for paper, metal, plastic or glass and are particularly useful in applications where the effect of a silicone coating is desired.

Photosensitizers allow one to utilize the gallates of the present invention at the longer wavelengths of light. The gallates may employ separate photosensitizers or sensitizers/ accelerators described in the prior art for sensitizing/accelerating cationic polymerization reactions. If a compound is serving as a photosensitizer only it must absorb light energy which can, in some form, be transferred to a gallate reacting species. Representative examples of photosensitizers that may be used include benzophenones, acetophenone acetals, benzoin ethers, substituted or nonsubstituted thioxanthones, fluorones, etc.

Additionally, photosensitizers may function as electron transfer donors in an oxidative chain as shown in U.S. Patent Application filed on even date herewith claiming priority of U.S. Provisional Application Ser. No. 60/137,115 "Accelerator/Sensitizers for Cationic Systems". In this embodiment, the crucial step is the formation of the excited state of the photosensitizer which is capable of electron donation to the ground state of the onium gallate. The formed radical cation of the photosensitizer deprotonates froming the oxy radical and an additional proton, thus accelerating the cationic polymerization. Representative, but nonlimiting examples of sensitizer/accelerators useful in the invention include naphthols, dihydroxynaphthalenes; polyhydroxy phenols, such as cresols, gallols, pyrogallols, etc.; di (C1–C10)alkoxynaphthalenes; C1–C10 alkoxyhydroxynaphthalenes; naphthyl glycidyl ethers and the like.

Because in the charge transfer reaction with the onium gallate the sensitizer/accelerator generates both free radicals and cations, it is possible to utilize a combination of free radical polymerizable and cationic polymerizable monomers. Examples of free radical polymerizable monomers include both monomers having one or more ethylenically unsaturated groups, such as vinyl or allyl groups, and polymers having terminal or pendant ethylenic unsaturation. Such compounds are easily identifiable to those skilled in the art and include acrylates.

If solvents are used to dissolve the photosensitizer/accelerator or an onium gallate they may be selected from the group yielding α-hydroxy alkylsubstituted carbon cenetered radicals upon UV induced cleavage. These radicals will further deprotonate and form a ketone. The proton released will participate in the cationic polymerization. Thus, the solvent may act as an accelerator as well. Some examples of the useful solvents include diacetone alcohol, 2-hydroxy-2-methyl-1-phenyl-propan-1 -one and the like.

In order to further illustrate the present invention and the advantages thereof, the following specific examples are given, it being understood that some are intended only as illustrative and in nowise limitative.

EXAMPLE 1

Preparation of Lithium Tetrakis(pentafluorophenyl)gallate

A 125 ml four-necked round bottom flask, equipped with a thermometer and two dropping funnels and magnetic stirrer, was employed. The assembly was dried beforehand under argon atmosphere. 80 mL of anhydrous pentane and 3.2 ml of bromopentafluorobenzene (25.67 mmol) were charged therein and then cooled to −78 C. 10 ml of a 2.5M solution of n-butyllithium (25.04 mmol) in hexane were added dropwise over 1.0 hr. The mixture was maintained under stirring for 3–5 hrs at −78%C. 10 ml of a solution of gallium chloride (6.25) mmol) in benzene (5.6 g of $GaCl_3$ dissolved in 50 mL benzene under argon atmosphere) were added dropwise to the above mixture over 1.0 hr. The mixture was kept for 3–5 hrs at −78%C. The cooling bath was removed. The reaction mixture was allowed to become ambient and was stirred overnight. The mixture was filtered, the filtrate was washed with hexane, then dried under reduced pressure at 60%C. A light yellow solid (containing LiCl) was thus obtained with a yield of 10–60%. Melting point is >300 C. The product was characterized by $^{19}$F-NMR (DMSO).

EXAMPLE 2

Preparation of Iodonium Tetrakis(pentafluorophenyl)gallate

In a 50 ml round-bottom flask, lithium tetrakis (pentafluorophenyl) gallate was dissolved in 15 ml $CH_2Cl_2$. The equal molar amount of iodonium chloride in 15 ml $CH_2Cl_2$ was added dropwise with stirring at room temperature. The reaction mixture became cloudy. After stirring for 2 hrs., the solvent was removed to yield a sticky residue. Chromatography on neutral alumina (a column of 3–5 cm in length was used) by elution with $CH_2Cl_2$ gave the desired iodonium tetrakis(pentafluorophenyl)gallate as a light yellow sticky liquid. Yield ranged from 70 to 85%. The structure was confirmed by [1] H-NMR and $^{19}$F-NMR.

Other compounds have been prepared according to the described procedure. Several are shown below.

General structure of tetrakispentafluorogallates

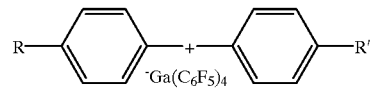

| where | R | R' | Molecular weight |
|---|---|---|---|
| Gallate 1 | $CH_3$ | $CH_3$ | 1047 |
| Gallate 2 | H | $O(CH_2)_3Si(CH_3)_3$ | 1149 |
| Gallate 3 | H | $OC_8H_{17}$ | 1147 |
| Gallate 4 | $C_{12}H_{25}$ | $C_{12}H_{25}$ | 1355 |

EXAMPLE 3

A. Solubility of the onium gallates in the cationically polymerized media

Formulations were prepared using the following epoxide functional resins:

DER-332—bisphenol A epoxy resin manufactured by Dow; standard in industry for a variety of UV and EB curable coatings, composites, etc.

SB oil—formulation containing cycloaliphatic epoxide (UVR-61 10 from Union Carbide), polyol (Tone-0310 from Union Carbide), epoxidized soybean oil (Vicoflex 7170 from Elf Atochem); forms an extremely flexible coating on metal.

GE Silicone—polyorganosiloxane resin 479-2008 from GE Silicones; main component of the paper release coating.

Formulations containing gallates were compared to formulations containing Rhodorsil-2074 (isopropylmethyliodonium tetrakis pentafluoroborate from Rhodia), OPPI (octyloxyphenylphenyliodonium hexafluoroantimonate from GE Silicones) and GE Silicones 479-1350 (didodecyliodonium hexafluoroantimonate). Solubility was assessed by mixing of 1 wt % of the initiator into the formulation and observing the mixture after ~1 hr at 60 C.

| Cationic initiator | Initiator appearance | Solubility in DER-332 | Solubility in SB oil | Solibility in Silicone |
|---|---|---|---|---|
| Rhodia 2074 | white powder | soluble | Soluble | soluble |
| OPPI | Yellowish powder | soluble | Soluble | mostly insoluble |
| Gallate 1 | Solidified wax | somewhat insoluble* | — | — |
| Gallate 2 | viscous wax | soluble | — | soluble |
| Gallate 3 | viscous oil | soluble | Soluble | soluble |
| Gallate 4 | viscous oil | soluble | — | soluble |
| GE 479-1350 | dark brown tar | soluble | — | soluble, but solution is hazy |

*Soluble after 24 hrs at 60 C.

EXAMPLE 4

B. UV curing behavior in cationically polymerizable formulations containing onium gallates.

All formulations were placed on a glass slide in a form of a bead of known weight. After UV exposure (Fusion 'H' bulb, standard medium pressure mercury arc lamp) cure was evaluated in three ways:

qualitative assessment (hardness, amount of the cured material)

% of cure by weight cure monitoring (CM) measurement of the fluorescence of the incorporated probe before and after the exposure. The difference between prior and after the exposure ratio of probe fluorescence is reported. According to the mechanism, a higher difference can be attributed to the better cure.

1) DER-332 Study

| Initiator | Qualitative assessment | % weight | CM probe ratio difference |
|---|---|---|---|
| 10 fpm | | | |
| Rhodia 2074 | through | 94 | 0.387 |
| OPPI | through/hard shell | 77 | 0.210 |
| Gallate 1 | through/hard shell | 90 | 0.477 |
| Gallate 2 | through/hard shell | 88 | 0.488 |
| Gallate 3 | through/hard shell | 90 | 0.453 |
| Gallate 4 | through/hard shell | 85 | 0.474 |
| Gallate 3, no probe | through | 100 | — |
| 20 fpm | | | |
| Rhodia 2074 | hard shell | 70 | 0.239 |
| OPPI | hard to moder. hard shell | 23 | 0.035 |
| Gallate 3 | hard shell | 35 | 0.108 |
| 44 fpm | | | |
| Rhodia 2074 | very soft skin | 22 | 0.038 |
| OPPI | very soft skin | 19 | 0.026 |
| Gallate 1 | very soft skin | 27 | 0.030 |
| Gallate 2 | gel* | — | 0.020 |
| Gallate 3 | soft skin | 21 | 0.017 |
| Gallate 4 | gel | — | 0.034 |
| Gallate 3, no probe | gel | — | — |

*Evaluation not possible

2) SB oil Study

| Initiator | Qualitative assessment | % weight | CM probe ratio difference |
|---|---|---|---|
| 10 fpm | | | |
| Rhodia 2074 | through | 98 | 0.392 |
| OPPI | through | 88 | 0.297 |
| Gallate 3 | through | 85 | 0.281 |
| 20 fpm | | | |
| Rhodia 2074 | soft shell | 25 | 0.193 |
| OPPI | soft shell | 26 | 0.135 |
| Gallate 3 | gel* | — | 0.168 |
| 44 fpm | | | |
| Rhodia | very soft skin* | — | 0.096 |

*Evaluation not possible

3) GE Silicone Study
Qualitative cure assessment

| Initiator, wt % | 10 fpm | 44 fpm | 120 fpm |
|---|---|---|---|
| Rhodia, 1 | Hard, glassy | Hard, glassy | Hard, glassy |
| Rhodia, 0.25 | Hard, glassy | Hard, glassy | Hard, glassy |
| OPPI, 1 | Soft, rubbery | Soft, rubbery | — |
| 479-1350, 1 | Hard, glassy | Hard, glassy | Hard, glassy |
| GE 479-1350, 0.25 | Hard, glassy | Hard, glassy | Hard, glassy, some liquid under bead |
| Gallate 3, 1 | Hard, glassy | Hard, glassy | Hard, glassy |
| Gallate 3, 0.25 | Hard, glassy | Hard, glassy | Hard, glassy |

The above data allows one to conclude that tetrakispentafluorogallates paired with various diaryliodonium cations are efficient cationic photoinitiators in the variety of cationically polymerizable or crosslinked media.

EXAMPLE 5

EB curing behavior of the cationically polymerizable formulations containing onium gallates.

EB curing was evaluated in DER-332 matrix at 1 wt % of the initiator. Administered dose is 10 Mrad at 200 mV beam voltage. Cure was qualitatively assessed by probing 5–10 mil thick strips of the polymerized material.

| Initiator | EB cure assessment |
|---|---|
| Rhodia | Hard polymer |
| Gallate 2 | Soft polymer |
| Gallate 3 | Soft polymer |

The above data shows that the gallates are EB initiators in the bisphenol A epoxy matrix.

Having described the invention in detail and by reference to preferred aspects thereof, it will be apparent that modifications and variations are possible without departing from the scope of the invention defined in the appended claims.

What is claimed is:

1. An onium salt having an anion of the formula $GaX_aR_b$, where X is a halogen atom or a hydroxy group, R is an aryl group, a and b represent integers of 0 to 4 and the sum of a and b is 4.

2. The onium salt of claim 1 wherein the onium salt includes a cation selected from the group consisting of iodonium, pyrylium, thiapyrylium, sulphonium, phosphonium, ferrocenium and diazonium ions.

3. The onium salt of claim 2 wherein X is halogen and a is 0, 1, 2, or 3 or X is hydroxy and a is 0, 1, or 2, at least one aryl group is a phenyl group substituted by at least one electron withdrawing group, or is an aryl radical having at least two aromatic rings.

4. The onium salt of claim 3 wherein onium salt includes an iodonium cation.

5. The onium salt of claim 2 wherein said salt is capable of initiating cationic polymeriziation upon exposure to actinic radiation alone or in the presence of a sensitizer.

6. The onium salt of claim 5 wherein the anion is selected from the group consisting of $[Ga(C_6F_5)_4]^-$, $[Ga(C_6H_4CF_3)_4]^-$, $[(C_6F_5)_2GaF_2]^-$, $(C_6F_5GaF_3)^-$, $[Ga(C_6H_3F_2)_4]^-$.

7. The onium salt of claim 4 wherein the iodonium cation is a diaryliodonium cation.

8. The onium salt of claim 3 wherein the onium salt includes a sulphonium cation.

9. A cationically polymerizable composition containing the onium salt of claim 1 and a cationically polymerizable or crosslinkable compound.

* * * * *